(12) United States Patent
Cook et al.

(10) Patent No.: US 10,932,896 B2
(45) Date of Patent: Mar. 2, 2021

(54) THIN-FILM CUFF FOR ENDOTHELIALIZATION OF ENDOVASCULAR GRAFTS

(71) Applicant: Monarch Biosciences, Inc., Los Angeles, CA (US)

(72) Inventors: Ian A. Cook, Los Angeles, CA (US); Colin Kealey, Los Angeles, CA (US); Vikas Gupta, Los Angeles, CA (US)

(73) Assignee: Monarch Biosciences, Inc., Los Angeles, CA (US)

( * ) Notice: Subject to any disclaimer, the term of this patent is extended or adjusted under 35 U.S.C. 154(b) by 110 days.

(21) Appl. No.: 15/605,754

(22) Filed: May 25, 2017

(65) Prior Publication Data

US 2017/0258569 A1 Sep. 14, 2017

Related U.S. Application Data

(63) Continuation of application No. PCT/US2016/027988, filed on Apr. 15, 2016.
(Continued)

(51) Int. Cl.
*A61F 2/07* (2013.01)
*A61F 2/06* (2013.01)
(Continued)

(52) U.S. Cl.
CPC .......... *A61F 2/07* (2013.01); *A61F 2/06* (2013.01); *A61F 2/844* (2013.01); *A61F 2/90* (2013.01); *A61L 27/025* (2013.01); *A61L 27/047* (2013.01); *A61L 27/06* (2013.01); *A61L 27/56* (2013.01); *A61L 31/022* (2013.01); *A61L 31/088* (2013.01); *A61F 2210/0014* (2013.01); *A61F 2210/0076* (2013.01);
(Continued)

(58) Field of Classification Search
None
See application file for complete search history.

(56) References Cited

U.S. PATENT DOCUMENTS 5,522,881 A 6/1996 Lentz
5,755,770 A 5/1998 Ravenscroft
(Continued)

OTHER PUBLICATIONS

Rigberg et al., "Thin-film nitinol (NiTi): A feasibility study for a novel aortic stent graft materials," Journal of Vascular Surgery, Aug. 2009, pp. 375-380, vol. 50—No. 2, Society of Vascular Surgery, Chicago, IL/USA.
(Continued)

*Primary Examiner* — Leslie Lopez
(74) *Attorney, Agent, or Firm* — Haynes and Boone LLP

(57) ABSTRACT

Methods and devices are provided for the use of thin-film cuffs on endovascular grafts. A method includes forming a fenestrated thin-film Nitinol sheet, expanding the fenestrated thin-film Nitinol sheet to expand the fenestrations, and attaching the expanded thin-film Nitinol sheet to a longitudinal end of a cover for an endovascular graft to form a cuff for the endovascular graft. The method may further include implanting the endovascular graft into a blood vessel. An endovascular graft may include a cover having a proximal and distal end, a proximal thin-film mesh cuff extending from the proximal end, and a distal thin-film mesh cuff extending form the distal end.

8 Claims, 9 Drawing Sheets

Related U.S. Application Data

(60) Provisional application No. 62/185,513, filed on Jun. 26, 2015, provisional application No. 62/148,689, filed on Apr. 16, 2015.

(51) Int. Cl.
| | |
|---|---|
| *A61F 2/90* | (2013.01) |
| *A61L 31/02* | (2006.01) |
| *A61L 27/06* | (2006.01) |
| *A61L 27/56* | (2006.01) |
| *A61F 2/844* | (2013.01) |
| *A61L 31/08* | (2006.01) |
| *A61L 27/02* | (2006.01) |
| *A61L 27/04* | (2006.01) |

(52) U.S. Cl.
CPC . *A61F 2220/005* (2013.01); *A61F 2220/0075* (2013.01); *A61F 2240/001* (2013.01)

(56) References Cited

U.S. PATENT DOCUMENTS

| | | |
|---|---|---|
| 6,221,079 B1 | 4/2001 | Magovern et al. |
| 6,786,919 B1 | 9/2004 | Escano et al. |
| 2005/0137677 A1 | 6/2005 | Rush |
| 2007/0173787 A1* | 7/2007 | Huang ............... A61F 2/82 604/891.1 |
| 2009/0132022 A1* | 5/2009 | Banas ............... A61F 2/82 623/1.13 |
| 2014/0249620 A1 | 9/2014 | Carman et al. |

OTHER PUBLICATIONS

Shayan et al., "An overview of thin film nitinol endovascular devices," Acta Biomaterialia, Mar. 2015, pp. 20-34, Elsevier Ltd, Philadelphia, PA/USA.

PCT International Search Report and Written Opinion of International Application No. PCT/US2016/027988, 12 pages, dated Jul. 26, 2016.

* cited by examiner

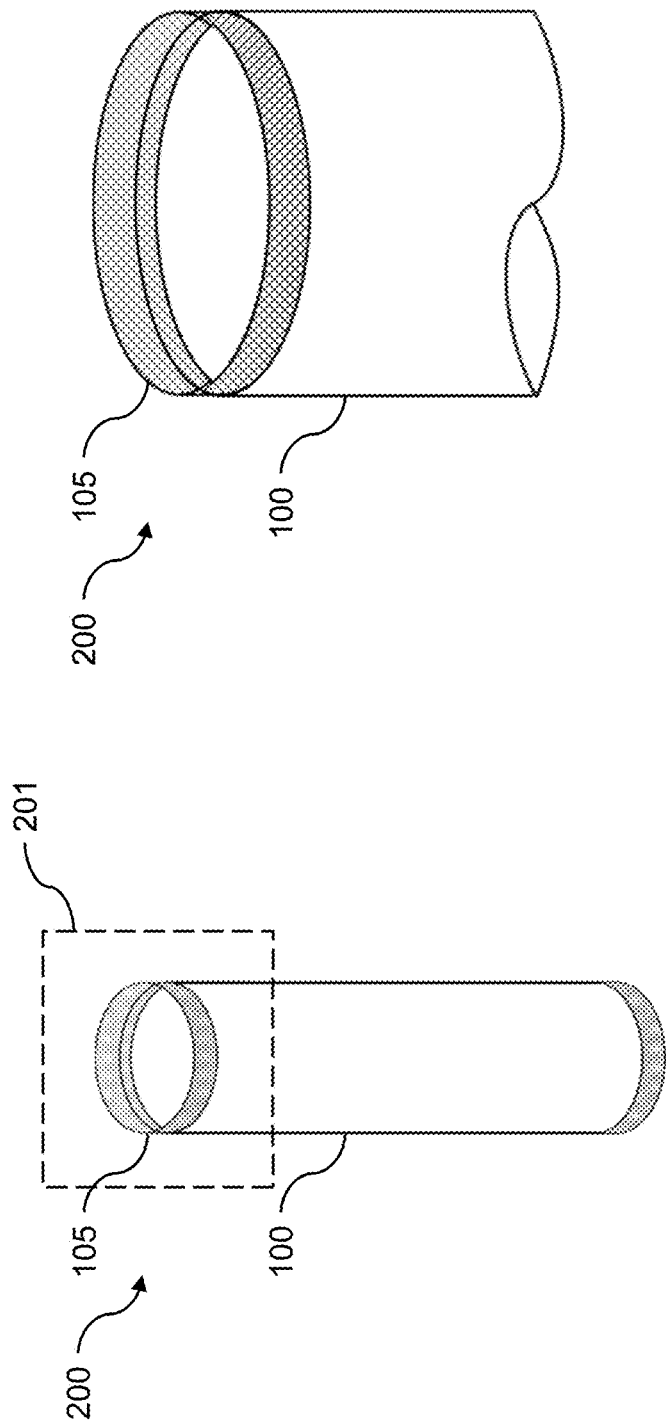

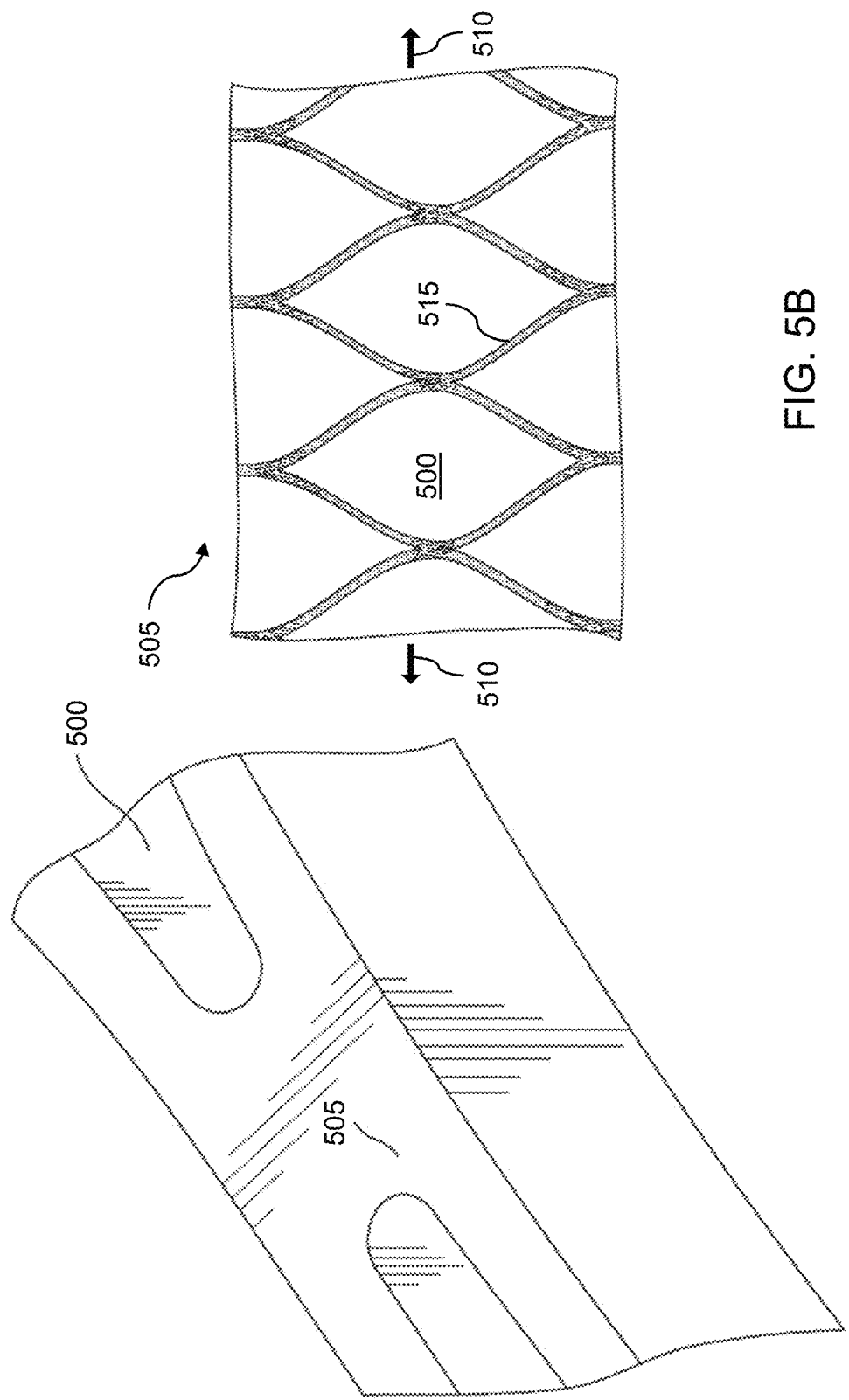

THIN-FILM CUFF FOR ENDOTHELIALIZATION OF ENDOVASCULAR GRAFTS

CROSS-REFERENCES TO RELATED APPLICATIONS

This application is a continuation of International Application No. PCT/US2016/027988, filed on Apr. 15, 2016, which claims the benefit of U.S. Provisional Application No. 62/148,689, filed on Apr. 16, 2015, and U.S. Provisional Application No. 62/185,513, filed on Jun. 26, 2015, which are hereby incorporated by reference in their entirety.

TECHNICAL FIELD

The present disclosure generally relates to intravascular devices and, more particularly, to the use of thin-film cuffs on endovascular grafts.

BACKGROUND

Aneurysms in large vessels such as an abdominal aortic aneurysm are relatively common in aging patients. The corresponding blood vessel may rapidly hemorrhage, perhaps mortally, if such aneurysms rupture. Given the extreme health risk, endovascular grafts have been developed to treat large-vessel aneurysms. A conventional endovascular graft typically comprises a stent that is covered by a fabric sheath such as a woven TEFLON® polytetrafluoroethylene (PTFE) sheath. The stent and associated sheath are compressed and delivered using a catheter and guide wire to the desired location. The woven sheath is impervious to blood flow such that the pressure on the aneurysm is significantly reduced, blood flow in the aneurysm sac is diminished so that it occludes, and the aneurysm thereby no longer poses imminent danger of rupture to the individual.

Although endovascular grafts are quite popular, complications may arise after implantation. A common complication is denoted as an endoleak, which involves blood continuing to pressurize the aneurysm despite proper positioning of the endovascular graft. For example, the proximal and/or distal ends of the endovascular graft may fail to seal against the vessel wall such that blood continues to flow into the aneurysm.

Other complications are related to anchoring of the graft to the blood vessel. Although many approaches to anchoring have been reduced to practice, problems include graft migration and perforation of the vessel or adjacent tissue.

Still other complications can arise if the endovascular graft inhibits flow of blood into vessels branching from the main vessel. For example, if a branch vessel such as the renal or mesenteric artery is occluded by an endovascular graft placed in the aorta, then ischemic damage to the kidneys or gastrointestinal tract may ensue.

Accordingly, there is a need in the art for improved endovascular grafts that prohibit endoleaks and securely anchor the graft to the vessel while preserving flow to branch vessels.

BRIEF DESCRIPTION OF THE DRAWINGS

FIG. 2A is a perspective view of the cover of FIG. 1A modified to include thin-film mesh cuffs to prevent endoleaks.

FIG. 2B is a partial cut away and expanded view of the thin-film cuffed cover of FIG. 2A.

FIG. 5A is a perspective view of a portion of a thin-film mesh cuff prior to expansion.

FIG. 5B is a plan view of a portion of a thin-film Nitinol mesh cuff after expansion.

Figure 1B:
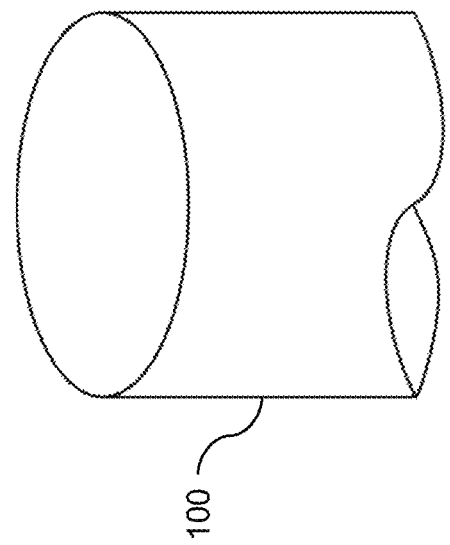
FIG. 1B is a partial cut away and expanded view of the cover of FIG. 1.

Embodiments of the present disclosure and their advantages are best understood by referring to the detailed description that follows. It should be appreciated that like reference numerals are used to identify like elements illustrated in one or more of the figures, in which the showings therein are for purposes of illustrating the embodiments and not for purposes of limiting them.

DETAILED DESCRIPTION

To prohibit endoleaks, an improved endovascular graft is provided with thin-film mesh cuffs at its proximal and/or distal ends. As used herein, a thin-film mesh (also referred to as a fenestrated thin-film or a fenestrated thin-film sheet) is defined to be less than 100 microns in thickness (e.g., between 3 and 30 microns in thickness). An example thin-film mesh comprises fenestrated thin-film Nitinol (TFN) although other thin-film mesh materials may be used to form the endovascular graft cuffs disclosed herein. The following discussion is thus directed to a thin-film Nitinol cuff without loss of generality. Example fenestrated thin-film Nitinol is disclosed in commonly-assigned International Application No. PCT/US2014/61836 (the "PCT application"), filed Oct. 22, 2014, which in turn claims the benefit of U.S. Provisional Application No. 61/894,826, filed Oct. 28, 2013. The contents of both of these applications are hereby incorporated by reference in their entirety.

To form a thin-film mesh, Nitinol (NiTi) may be sputtered onto patterned silicon wafers. The patterned mesh may then be removed using a lift-off process by etching away a sacrificial layer such as a chromium layer to form a two-dimensional (2D) thin-film mesh. A cover (e.g., a woven fabric cover) for an endovascular graft is impermeable or substantially impermeable and may be very robust. A sheet of fenestrated thin-film Nitinol may thus be rolled about the distal and proximal ends of the cover and fastened using, for example, an adhesive (e.g., glue) or stiches.

Alternatively, this lift-off process is combined with multiple-layer depositions of Nitinol separated by layers of sacrificial material to fabricate cylindrical a thin-film mesh, which are three-dimensional (3D) in the sense that two layers are joined together along their longitudinal edges such that the resulting joined layers may be opened up to form a cylinder. For example, the three-dimensional fabrication techniques disclosed in the PCT application may be used to manufacture a circumferential ring of thin-film Nitinol, which would then be fastened to the cover.

The thin-film mesh may be attached to one or both ends of a woven fabric cover such as a woven TEFLON® polytetrafluoroethylene (PTFE) cover. In other embodiments, the thin-film mesh may be attached to other impermeable covers or substantially impermeable covers (e.g., less permeable compared to the thin-film mesh) suitable as endovascular grafts. The following discussion is thus directed to woven fabric covers without loss of generality.

Figure 1A:
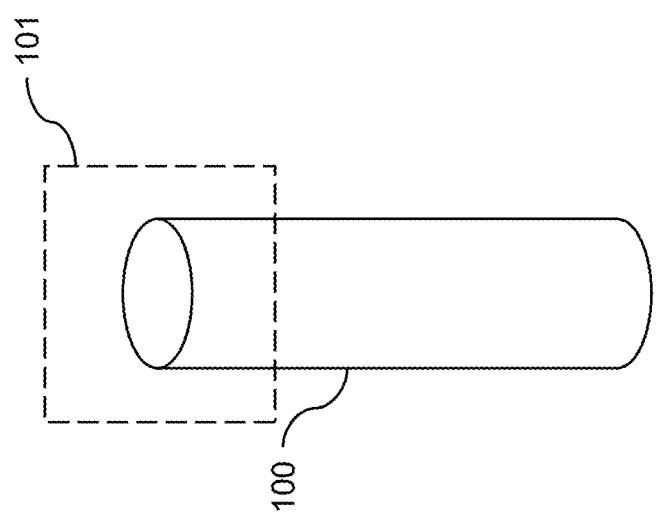
FIG. 1A is a perspective view of a cover for an endovascular graft.

A conventional tubular woven fabric cover 100 (also referred to as woven fabric graft) for an endovascular graft is shown in FIG. 1A. An expanded view of an end portion 101 of woven fabric cover 100 is shown in FIG. 1B. The distal and proximal ends of cover 100 are prone to developing endoleaks after implantation as discussed earlier.

To prevent or substantially eliminate the risk of endoleaks, a thin-film mesh cuff 105 (also referred to as a thin-film mesh addition) is attached to the proximal and/or distal ends of cover 100, as shown by a thin-film cuffed cover 200 (also referred to as thin-film cuffed graft) in FIG. 2A. An expanded view of an end portion 201 of thin-film cuffed cover 200 is shown in FIG. 2B. In an example, thin-film mesh cuff 105 is attached to cover 100 by an adhesive, such as glue. In another example, thin-film mesh cuff 105 is attached to cover 100 by stiches. In other examples, thin-film mesh cuff 105 is fastened to cover 100 using other fastening methods as appropriate.

Figure 3A:
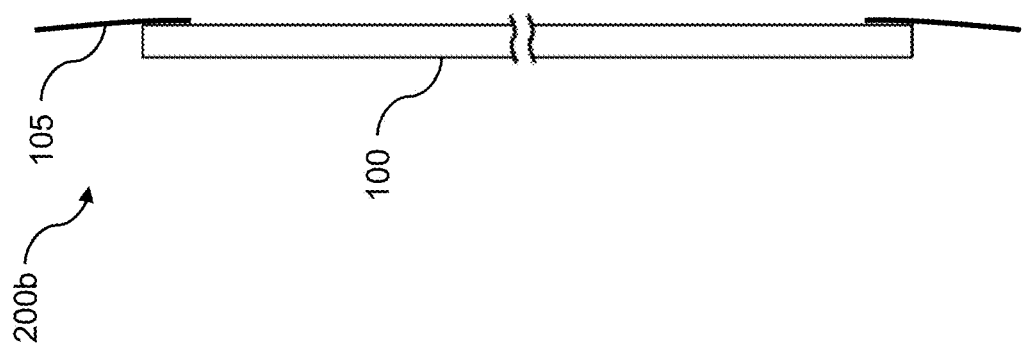
FIG. 3A is a cross-sectional view of the thin-film cuffed cover having thin-film mesh cuffs attached to the luminal surface of the cover.
Figure 3B:
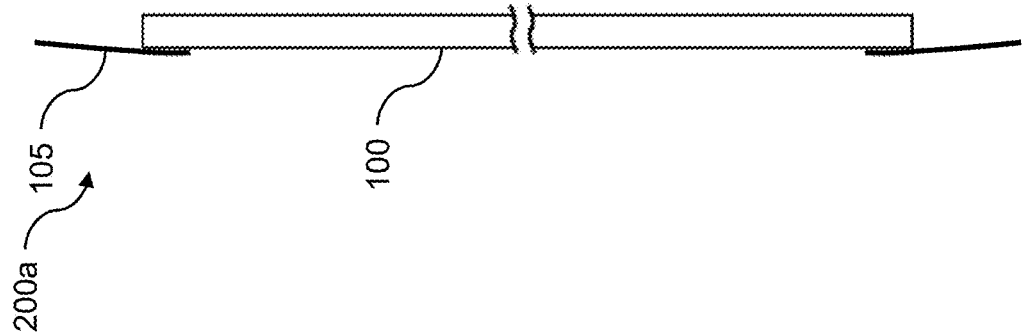
FIG. 3B is a cross-sectional view of the thin-film cuffed cover of FIG. 2A having thin-film mesh cuffs attached to the outer surface of the cover.
Figure 3C:
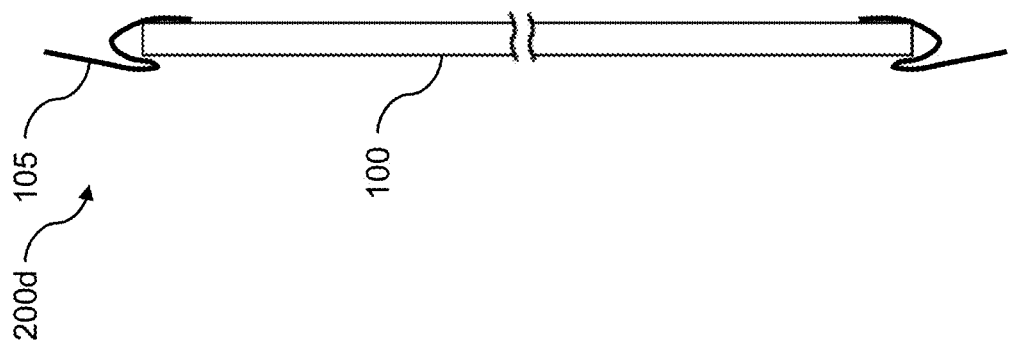
FIG. 3C is a cross-sectional view of the thin-film cuffed cover of FIG. 2A having thin-film mesh cuffs attached to the outer surface of the cover and folded to attach to the luminal surface of the cover.
Figure 3D:
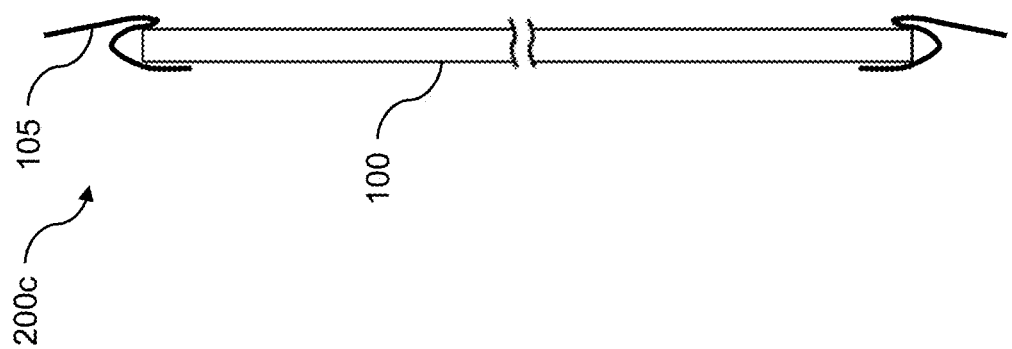
FIG. 3D is a cross-sectional view of the thin-film cuffed cover of FIG. 2A having thin-film mesh cuffs attached to the luminal surface of the cover and folded to attach to the outer surface of the cover.

FIGS. 3A-D are cross-sectional views of thin-film cuffed cover 200 in which thin-film mesh cuffs 105 are attached to cover 100. Cuff 105 may attach to the luminal or outer surface of cover 100. As shown in FIG. 3A, on one or both ends of cover 100. For example, as shown by the cross-sectional view of thin-film cuffed cover 200A in FIG. 3A, thin-film cuffed cover 200A has thin-film mesh cuffs 105 attached to the luminal surface of cover 100 on each side. In another example, as shown by the cross-sectional view of thin-film cuffed cover 200B in FIG. 3B, thin-film cuffed cover 200B has thin-film mesh cuffs 105 attached to the outer surface of cover 100 on each side.

In an alternative embodiment, cuff 105 may be folded such that it is attached to both the luminal and outer surface as indicated by dotted line 110. For example, as shown by the cross-sectional view of thin-film cuffed cover 200C in FIG. 3C, thin-film cuffed cover 200C has thin-film mesh cuffs 105 that attach to the luminal surface of cover 100 and fold to attach to the luminal surface of cover 100 on each side. In another example, as shown by the cross-sectional view of thin-film cuffed cover 200D in FIG. 3D, thin-film cuffed cover 200D has thin-film mesh cuffs 105 that attach to the outer surface of cover 100 and fold to attach to the outer surface on each side.

Figure 4A:
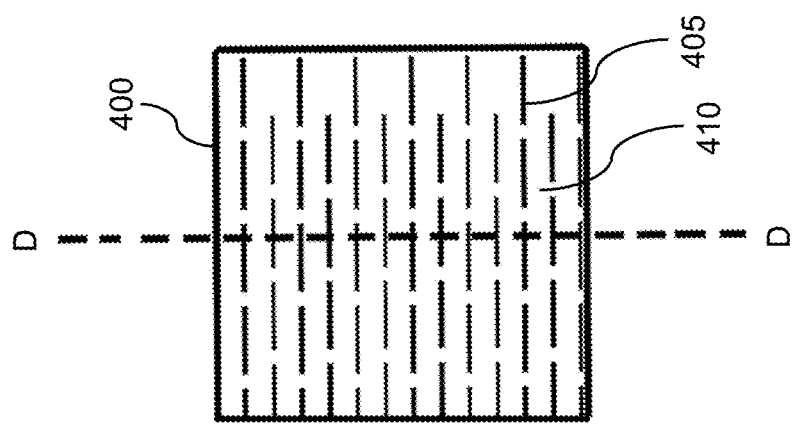
FIG. 4A is a plan view of an etched semiconductor wafer for making a thin-film mesh cuff.
Figure 4B:
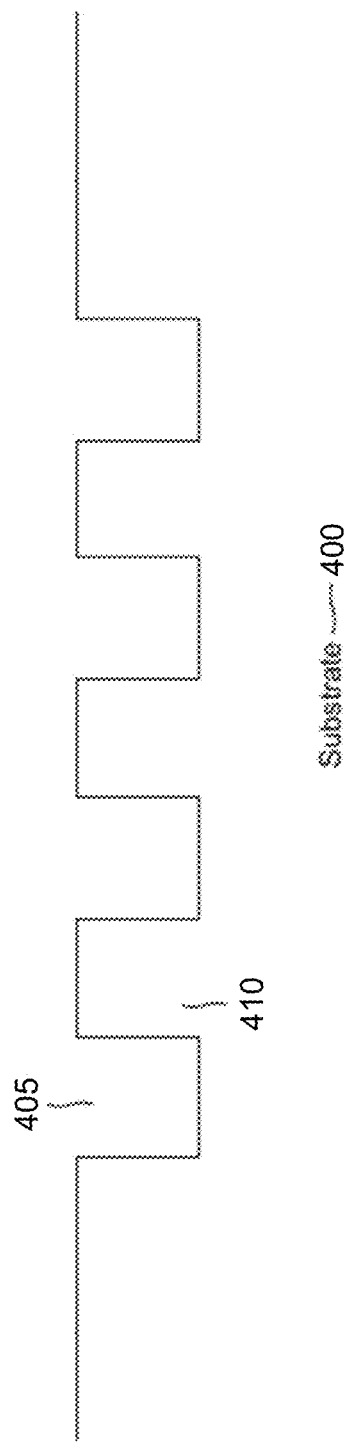
FIG. 4B is a cross-sectional view of the wafer of FIG. 4A along lines D:D.

The longitudinal extent of mesh cuff 105 depends upon the application but it will generally extend several millimeters from a longitudinal end of cover 100. In one embodiment, mesh cuff 105 may be formed using a deep-reactive ion etched semiconductor wafer as described in the PCT application. FIG. 4A is a plan view of a substrate such as an etched wafer 400 formed by using a deep reactive-ion etching (DRIE) process. Grooves 405 are separated by lands 410. Rows of grooves 405 are displaced with respect to adjacent rows of grooves 405 such that a groove 405 in one row is longitudinally displaced by approximately 50% with regard to the neighboring grooves in the immediately-adjacent grooves. FIG. 4B illustrates a cross-section of etched wafer 400. Grooves 405 are separated by lands 410. The width of lands 410 may be 1 to 30 microns (e.g., between 4 and 30 microns, between 4 and 20 microns, between 1 and 20 microns, approximately 10 microns, etc.) in some embodiments. Similarly, the width of grooves 405 may be 1 to 30 microns (e.g., between 4 and 30 microns, between 4 and 20 microns, between 1 and 20 microns, approximately 10 microns, etc.). The longitudinal extent of each groove 405 may range from a few microns to approximately 500 microns (e.g., between 100 microns and 500 microns, between 100 microns and 400 microns, between 100 microns and 300 microns, between 150 microns and 400 microns, etc.).

Nitinol may then be deposited on etched wafer 400 to a thickness of approximately 1 to 30 microns (e.g., between 4 and 30 microns, between 4 and 20 microns, between 1 and 20 microns, approximately 10 microns, etc.) and then lifted off. Grooves 405 will then be duplicated on the resulting patterned thin-film Nitinol sheet as corresponding longitudinally-extending fenestrations. The resulting patterns of fenestrations may also be denoted as a fiche in that the fenestrations are in collapsed form prior to an expansion of the Nitinol sheet. Just like a microfiche, each fiche or pattern of fenestrations effectively codes for the resulting fenestrations when the stent cover is expanded to fully open up the fenestrations.

This may be better appreciated with regard to FIG. 5A, which shows two fenestrations 500 in a portion of a thin-film mesh 505 prior to expansion. In FIG. 5B, mesh 505 is expanded in the lateral direction 510 (also referred to as the axis of expansion of mesh 505) orthogonal to the longitudinal axis of fenestrations 500 (also referred to as the longitudinal direction or long axis of fenestrations 500) such that fenestrations 500 open up into a "chain-link" fence pattern of diamond-shaped fenestrations. In some embodiments, the expansion may extend mesh 505 in a range from 100% to 800%. Thin-film mesh 505 as fabricated (prior to expansion) has fenestrations 500 that duplicate grooves 405 of wafer 400, and struts 515 that duplicate lands 410 of wafer 400. Accordingly, prior to expansion, the longitudinal extent of each fenestration 500 may range from a few microns to approximately 500 microns (e.g., between 100 microns and 500 microns, between 100 microns and 400 microns, between 100 microns and 300 microns, between 150 microns and 400 microns, etc.). After expansion, the longitudinal extent of each fenestration 500 decreases (e.g., between 5% and 20%) while the width of each fenestration increases (e.g., between 100 to 800%). Struts 515 may have a thickness of between 1 and 30 microns (e.g., between 4 and 30 microns, between 4 and 20 microns, between 1 and 20 microns, approximately 10 microns, etc.) prior to and after expansion.

Cuff 105 may include fenestrations having a longitudinal axis that is parallel to the longitudinal axis of cover 100 (also referred to as the longitudinal direction of cover 100). Accordingly, cuff 105 may be fabricated to be expandable in the radial direction. When cuff 105 is expanded, a radius of the circular cross-section of cuff 105 may be equal or approximately equal to a radius of the circular cross-section of cover 100. Alternatively, cuff 105 may include fenestrations having a longitudinal axis that is orthogonal to the longitudinal axis of cover 100. Accordingly, cuff 105 may be expandable in the longitudinal axis of cover 100.

The resulting high pore density, fenestrations per square mm, (e.g., between 81 and 1075 pores per $mm^2$, between 134 and 227 pores per $mm^2$, between 81 and 227 pores per $mm^2$, etc.) and low metal coverage (e.g., between 19 and 66%, between 24 and 36%, between 19% and 36%, etc.) is very advantageous with regard to promoting a planar deposition of fibrin followed by a rapid endothelialization. In this fashion, cuffs 105 (shown in FIGS. 2A, 2B, 3A, 3B, 3C, and 3D) are incorporated into the blood vessel endothelial lining, which thus seals the ends of graft 200 to prevent endoleaks. It will be appreciated that other fenestration shapes may be used in alternative embodiments.

Thin-film meshes such as thin-film mesh 505, orientation of fenestrations, and various parameters for thin-film meshes relating to fenestrations such as fenestrations 505, struts such as struts 515, pore density, percent metal coverage, strut angle, and other features of the thin-film meshes may be implemented in accordance with the techniques described in U.S. Provisional Application No. 62/148,689, previously referenced herein.

In addition to prevention of endoleaks, the biological seal of the endothelium also serves to anchor graft 200. As the body incorporates the thin-film Nitinol elements of graft 200 into the vessel wall, graft 200 is stabilized mechanically, thereby mitigating the issue of graft migration. Notably, this is accomplished without damage to the vessel wall or adjacent structures.

Data from an animal model have demonstrated that the placement of a thin film of Nitinol over a branch vessel (i.e., over the ostium of the lumbar artery where it branches from the abdominal aorta) advantageously does not impede adequate flow in the branch vessel, as described in Ding et al., Preclinical Testing of a Novel Thin Film Nitinol Flow-Diversion Stent in a Rabbit Elastase Aneurysm Model, American Journal of Neuroradiology, 2016; 37(3):497-501, which is incorporated herein by its entirety.

Figure 6:
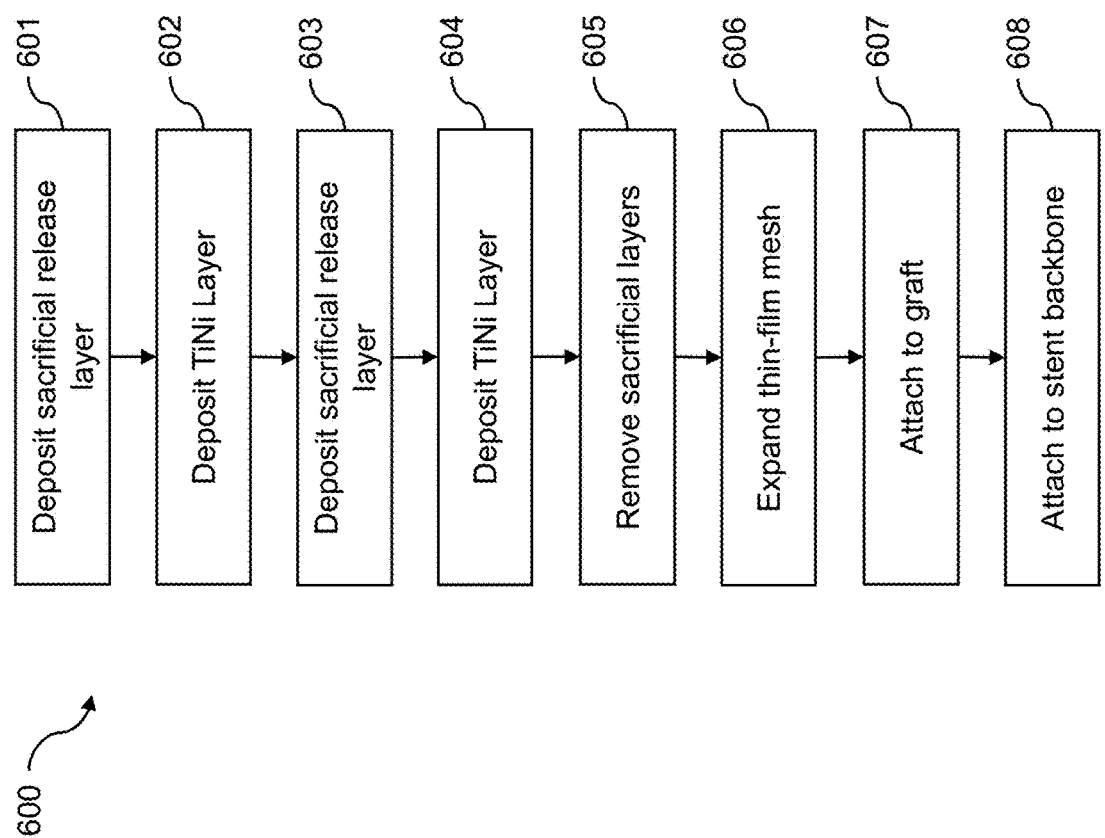
FIG. 6 illustrates a method for forming the thin-film cuffed cover of FIG. 2A using three-dimensional thin-film meshes.

FIG. 6 illustrates a method 600 for forming thin-film cuffed cover 200 using a three-dimensional thin-film mesh.

At step 601, a first sacrificial layer (e.g., a lift-off or release layer) of Cr (or other sacrificial or barrier layers) is deposited on a silicon substrate (e.g., silicon wafer substrate 400), for example, in a sputtering chamber while the substrate is held at high vacuum or under ultra-high vacuum, using e-beam evaporation or PECVD. When subsequently etched away, the lift-off layer may release the finished product such as cuff 105 from the substrate (e.g., silicon wafer substrate 400) and may thus be referred to as a release layer. The lift-off layer may be 1700 to 3000 Angstroms of sputter-deposited chromium.

Prior to the deposition of the lift-off layer, the substrate may first (e.g., before deposition) be prepared in step 601 by etching (using, for example, dry etching or DRIE) grooves or trenches that will correspond to fenestrations 500 of the web fiche pattern or other surface features that may correspond to structures (e.g., mesh fenestrations) of a finished product such as cuff 105. Step 601 and subsequent steps 602 through 604 may all be performed while the substrate continues to be held under a vacuum in a sputtering chamber and without removing the vacuum (or removing the substrate wafer or device from the vacuum chamber) until all depositions are completed.

At step 602, a first layer of NiTi may be deposited using one or more sputtering or other techniques. An example thickness of this first layer (as well as the second layer of NiTi) is between 3 and 30 microns in thickness (e.g., 3 to 5 microns).

At step 603, a second sacrificial layer of Cr (or other sacrificial or barrier layers) may be deposited on the silicon substrate (e.g., silicon wafer substrate 400), for example, in a sputtering (or vacuum) chamber while the substrate continues to be held at high vacuum or under ultra-high vacuum, using e-beam evaporation or PECVD. A shadow mask may be placed over the substrate and the previously deposited layers such as the release layer and the first NiTi layer prior to depositing the second sacrificial layer to protect covered (or blocked) areas from deposition of the second Cr sacrificial layer (or other sacrificial or barrier layers). The shadow mask may be removed from the substrate and the accumulated deposited layers after depositing the second sacrificial layer.

In some embodiments, an aluminum bonding layer is applied using a reverse mask to prevent formation of an oxidized surface layer on the first NiTi layer. It will be appreciated that bonding of one NiTi layer onto another can be problematic if an oxidized surface layer is formed on the first NiTi layer because this surface layer inhibits the bonding of one NiTi layer to another. The reverse mask (as implied by the name) is the complement of the shadow mask used to form the second sacrificial layer. In other words, the reverse mask covers the second sacrificial layer and exposes the uncovered areas of the first NiTi layer. Aluminum may then be sputtered through the reverse mask to form the bonding layer. Since the bonding layer is applied, the first NiTi layer may be exposed to the atmosphere between the masking with the shadow mask and the subsequent masking with the reverse mask. In this fashion, manufacturing costs are lowered in that the applications of the masks is greatly aided by performing the mask applications outside of the vacuum chamber using, for example, conventional semiconductor pick-and-place equipment. Alternatively, the first NiTi layer may be maintained in a vacuum or an ultra-high vacuum until a second layer of NiTi is deposited, including during the application and removal of the shadow mask.

At step 604, a second layer of NiTi may be deposited using one or more sputtering or other techniques. At this step, deposition of the second layer of NiTi may result in the second layer of NiTi bonding to the first layer of NiTi at those areas left exposed by the second sacrificial layer, forming, for example, bonds at the edges of cuff 105.

In embodiments in which the bonding layer is utilized, wafer 400 may be heated to approximately 500 to 600 degrees prior to removal of the lift-off and sacrificial layers at step 506. Such heating partially melts the aluminum, which then becomes very reactive despite the formation of some aluminum oxides. The molten un-oxidized aluminum is very reactive and chemically bonds to the NiTi layers, resulting in a very secure bond, despite the formation of an oxidized NiTi surface on the first NiTi layer.

At step 605, removal of the sacrificial layers (e.g., the first sacrificial or release layer and the second sacrificial layer) may be performed using a wet etch and may be performed after allowing the vacuum chamber to repressurize or after removing substrate 400 from the vacuum chamber. Etching the sacrificial layers may release cuff 105 from the substrate and may remove interior layers such as the second sacrificial layer. The etch may comprise soaking silicon substrate wafer 400 and the deposited layers in a solution, for example, of Cr etch, and may create a lumen where sacrificial layers are removed between the first and second NiTi layers that are joined at the edges.

At step 606, cuff 105 is expanded such that fenestrations 500 open up into a "chain-link" fence pattern of diamond-shaped fenestrations. Further processing may be performed, such as shaping cuff 105 including, for example, shaping cuff 105 into a more cylindrical shape by insertion of a mandrel into the lumen. With cuff 105 in the desired shape, the NiTi layers may be crystallized. Blstepocks 601-606 are further described in the PCT application.

At step 607, cuff 105 is attached to fabric woven cover 100 to form a thin-film cuffed cover such as thin-film cuffed cover 200. Cuff 105 may be attached to cover 100 by an adhesive, such as glue, by stiches, or other fastening methods as appropriate.

At step 608, thin-film cuffed cover 200 is attached to a stent backbone. The covered stent with thin-film cuffs may then be implanted using a catheter.

Figure 7:
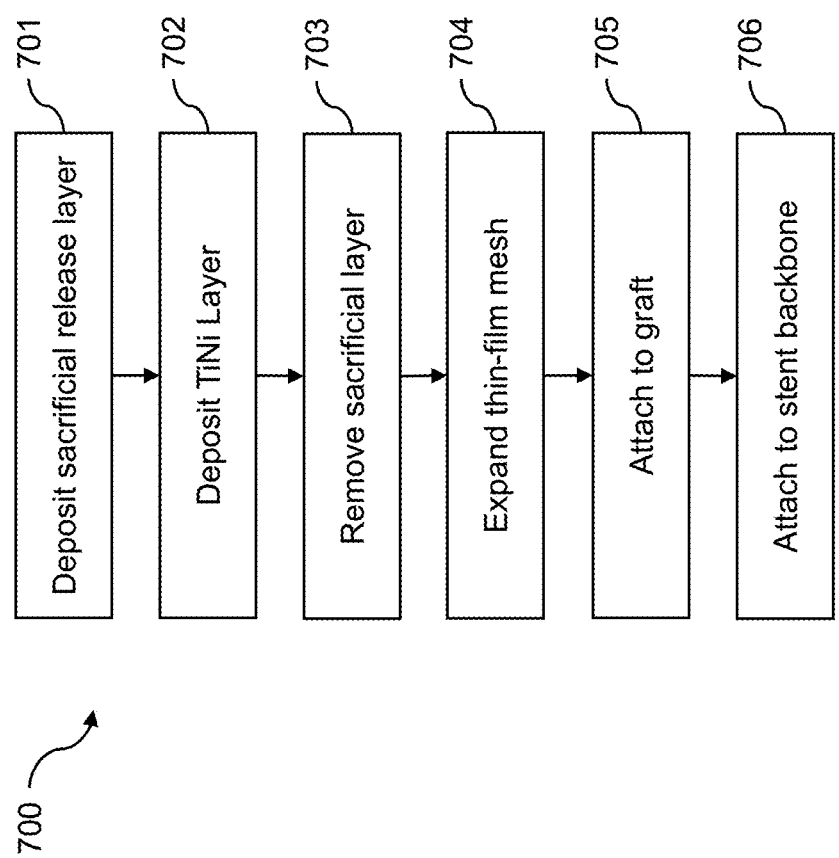
FIG. 7 illustrates a method for forming the thin-film cuffed cover of 2A using two-dimensional thin-film meshes.

FIG. 7 illustrates a method 700 for forming thin-film cuffed cover 200 using two-dimensional thin-film meshes.

At step 701, a sacrificial layer (e.g., a lift-off or release layer) of Cr (or other sacrificial or barrier layers) is deposited on a silicon substrate (e.g., silicon wafer substrate 400), for example, in a sputtering chamber while the substrate is held at high vacuum or under ultra-high vacuum, using e-beam evaporation or PECVD. Prior to the deposition of the lift-off layer, the substrate may first (e.g., before deposition) be prepared in step 701 by etching (using, for example, dry etching or DRIE) grooves or trenches that will correspond to fenestrations 500 of the web fiche pattern or other surface features that may correspond to structures (e.g., mesh fenestrations) of a finished product such as cuff 105.

At step 702, a layer of NiTi may be deposited using one or more sputtering or other techniques. An example thickness of this first layer (as well as the second layer of NiTi) is between 3 and 30 microns in thickness (e.g., 3 to 5 microns).

At step 703, removal of the sacrificial layers may be performed using a wet etch and may be performed after allowing the vacuum chamber to repressurize or after removing substrate 400 from the vacuum chamber. Etching the sacrificial layers may release cuff 105 from the substrate. The etch may comprise soaking silicon substrate wafer 400 and the deposited layers in a solution, for example, of Cr etch.

At step 704, cuff 105 is expanded such that fenestrations 500 open up into a "chain-link" fence pattern of diamond-shaped fenestrations. Further processing may be performed, such as shaping cuff 105 including, for example, shaping cuff 105 into a more cylindrical shape by annealing on a mandrel. With cuff 105 in the desired shape, the NiTi layers may be crystallized.

At step 705, cuff 105 is attached to fabric woven cover 100 to form a thin-film cuffed cover such as thin-film cuffed cover 200. Cuff 105 may be attached to cover 100 by an adhesive, such as glue, by stiches, or other fastening methods as appropriate.

At step 706, thin-film cuffed cover 200 is attached to a stent backbone. The covered stent with thin-film cuffs may then be implanted using a catheter.

Thin-film mesh cuff 105 formed using the techniques described herein is planar with regard to the wire intersections. In that regard, the columnar fenestrations may be expanded into diamond shapes (e.g., having a length of approximately 300 microns and a width of approximately 150 microns). In contrast, the resulting wire forming the diamond-shaped fenestrations is only 4 to 30 microns in thickness. Each "corner" of the diamond-shaped fenestration is thus relatively flat such that a null region with regard to fluid flow is formed at each corner. This may be better appreciated with regard to FIG. 5B, which shows the diamond-shaped fenestrations that result upon expansion. As shown in the close-up view in FIG. 5A, for the adjacent longitudinal ends of two diamond-shaped fenestrations 500, the thin-film mesh 505 forms flat interstices that are advantageously conducive to the desired clotting process so that flow diversion of aneurysm is safely achieved. Such interstices are absent in a conventional wire mesh because of the weaving of the relatively coarse wire.

Embodiments described herein illustrate but do not limit the disclosure. It should also be understood that numerous modifications and variations are possible in accordance with the principles of the present disclosure. Accordingly, the scope of the disclosure is best defined only by the following claims.

What is claimed is:

1. An endovascular graft, comprising:
a tubular cover extending along a longitudinal axis and having a circular cross-section,
wherein the tubular cover is at least one of an impermeable cover or a woven fabric cover; and
a fenestrated thin-film cuff having a circular cross-section and attached to a longitudinal end of the tubular cover such that the fenestrated thin-film cuff is attached to the tubular cover, the fenestrated thin-film cuff is formed from a first Nitinol layer deposited on a second Nitinol layer with a sacrificial layer removed from between the first and the second Nitinol layers.

2. The endovascular graft of claim 1, further comprising:
an additional fenestrated thin-film cuff having a circular cross-section and extending from an opposing longitudinal end of the tubular cover.

3. The endovascular graft of claim 1, wherein the fenestrated thin-film cuff comprises a fenestrated thin-film Nitinol sheet.

4. The endovascular graft of claim 1, wherein the fenestrated thin-film cuff comprise a two-dimensional fenestrated thin-film sheet.

5. The endovascular graft of claim 1, wherein the fenestrated thin-film cuff comprise a three-dimensional fenestrated thin-film sheet having a circular cross-section with a radius that is equal or approximately equal to a radius of a circular cross-section of the tubular cover.

6. The endovascular graft of claim 1, wherein the fenestrated thin-film cuff has a thickness of between 4 and 30 microns, wherein each fenestration of the fenestrated thin-film cuff has a length of between 100 and 500 microns before expansion, and wherein each strut of the fenestrated thin-film cuff has a width of between 4 microns and 30 microns.

7. The endovascular graft of claim 1, wherein the fenestrated thin-film cuff is attached to a luminal surface of the tubular cover and/or an outer surface of the tubular cover.

8. The endovascular graft of claim 1, further comprising:
a stent backbone, wherein the thin-film cuffed cover is attached to the stent backbone.

* * * * *